US010460423B2

(12) United States Patent
Athavale et al.

(10) Patent No.: US 10,460,423 B2
(45) Date of Patent: Oct. 29, 2019

(54) SYSTEM AND METHOD FOR MEDICAL IMAGE QUALITY ENHANCEMENT USING MULTISCALE TOTAL VARIATION FLOW

(71) Applicant: SUNNYBROOK HEALTH SCIENCES CENTRE, Toronto (CA)

(72) Inventors: Prashant Athavale, Toronto (CA); Adrian Nachman, Toronto (CA); Graham Wright, Toronto (CA); Perry Radau, Toronto (CA)

( * ) Notice: Subject to any disclaimer, the term of this patent is extended or adjusted under 35 U.S.C. 154(b) by 221 days.

(21) Appl. No.: 14/766,587

(22) PCT Filed: Feb. 7, 2014

(86) PCT No.: PCT/CA2014/050084
§ 371 (c)(1),
(2) Date: Aug. 7, 2015

(87) PCT Pub. No.: WO2014/121400
PCT Pub. Date: Aug. 14, 2014

(65) Prior Publication Data
US 2015/0371372 A1    Dec. 24, 2015

Related U.S. Application Data

(60) Provisional application No. 61/762,787, filed on Feb. 8, 2013.

(51) Int. Cl.
*G06K 9/00* (2006.01)
*G06T 5/00* (2006.01)
(Continued)

(52) U.S. Cl.
CPC ............ *G06T 5/002* (2013.01); *A61B 5/055* (2013.01); *A61B 5/7203* (2013.01);
(Continued)

(58) Field of Classification Search
CPC .. G06T 5/002; G06T 5/20; G06T 7/33; G06T 2207/10088; G06T 2207/20016; A61B 5/055; A61B 5/7203; G01R 33/5608
See application file for complete search history.

(56) References Cited

U.S. PATENT DOCUMENTS 7,564,585 B2 *  7/2009  Berkner ................ H04N 1/405
                                                    358/1.9
7,889,950 B2 *  2/2011  Milanfar ................. G06K 9/40
                                                    348/441

OTHER PUBLICATIONS

International Search Report and Written Opinion dated Jun. 11, 2014, in connection with PCT/CA2014/050084.
(Continued)

*Primary Examiner* — Shefali D Goradia
(74) *Attorney, Agent, or Firm* — Quarles & Brady LLP

(57) ABSTRACT

Methods for representing multiple scales in an image using a variational algorithm are provided. An iterative decomposition of an image into a total variation ("TV") part, which may be a weighted TV ("$TV_\alpha$") part, and a residual part motivates the design and use of a partial differential equation that may be referred to as a multiscale total variation flow, or multiscale weighted total variation flow. This produces a multiscale representation of the image. The speed of this decomposition can be controlled with a user-defined function, and is fast enough to allow for real-time applications of denoising and image registration.

14 Claims, 4 Drawing Sheets

(51) Int. Cl.
*A61B 5/055* (2006.01)
*G01R 33/56* (2006.01)
*A61B 5/00* (2006.01)
*G06T 5/20* (2006.01)
*G06T 7/33* (2017.01)

(52) U.S. Cl.
CPC ............ *G01R 33/5608* (2013.01); *G06T 5/20* (2013.01); *G06T 7/33* (2017.01); *G06T 2207/10088* (2013.01); *G06T 2207/20016* (2013.01)

(56) References Cited

OTHER PUBLICATIONS

Chan, T.F., et al., "Multiscale Total Variation and Multiscale Anisotropic Diffusion Algorithms for Image Denoising", submitted to Applied and Computational Harmonic Analysis (2008); http://www.mth.msu.edu/--Ywang/preprints/mtv-denoising-chanwangzhou.pdf (retrieved on May 2014).

Wang, Yang, et al., "Multiscale Total Variational Algorithms for Denoising Natural Color Photos in Digital Photography."; http//www.math.msu.edu/~ywang/preparints.html (last updated Feb. 2011, retrieved on May 2014).

Yang, Junfeng, eta l., "A Fast Algorithm for Edge-Preserving Variational Multichannel Image Restoreation", UCLA CAM Report 08-50 (2009); p. 1-19; ftp://ftp.math.ucla/edu/pub/camrepreot/cam08-50.pdf (retrieved on May 2014).

Paquin, Dana C., et al., "Multiscale Image Registration", Mathematical biosciences and engineering, vol. 3, Nov. 2, 2006; http://www.math.umd.edu/!dlevy/papers/registration.pdf (retrieved on May 2014).

\* cited by examiner

SYSTEM AND METHOD FOR MEDICAL IMAGE QUALITY ENHANCEMENT USING MULTISCALE TOTAL VARIATION FLOW

CROSS-REFERENCE TO RELATED APPLICATIONS

This application represents the national stage entry of PCT International Application No. PCT/CA2014/050084 filed on Feb. 7, 2014, which claims the benefit of U.S. Provisional Patent Application Ser. No. 61/762,787 filed on Feb. 8, 2013, the disclosures of which are hereby incorporated by reference in their entirety for all purposes.

BACKGROUND OF THE INVENTION

The field of the invention is systems and methods for medical image quality enhancement. More particularly, the invention relates to systems and methods for enhancing medical images using a multiscale decomposition framework.

Medical images contain image structures of varying scales, with different scales representing different components. For example, in cardiac images, left ventricle, myocardium, and blood pool are large-scale structures, whereas infarct and noise are represented by relatively small-scale structures. Thus, extracting different scales in an image (i.e., multiscale image representation) is a valuable tool in medical image processing.

There are various multiscale representation techniques based on different image decomposition algorithms and denoising methods. Gaussian blurring with varying standard deviation can be considered as a multiscale representation, but it diffuses the image isotropically, thereby diffusing main edges. On the other hand, inverse scale representations based on variational formulations preserve edges, but tend to be time consuming and thus unsuitable for real-time applications.

Noise present in medical images makes it difficult for clinicians to use these images for diagnosis. It also makes it problematic in many image processing algorithms, including image registration. Thus, denoising is used as a preprocessing step before most medical image processing techniques. Nevertheless, edges present in medical images are very important and must not be diffused during the denoising step. For instance, in denoising magnetic resonance images, it is important to preserve edges. Gaussian filtering, being isotropic in nature, smoothes all edges, hence anisotropic filters such as the bilateral filter are commonly used in medical imaging applications.

It would therefore be desirable to provide a method for denoising medical images that not only preserves edge features in the original image, but also achieves denoising in less time than currently available techniques so as to provide for real-time denoising applications.

SUMMARY OF THE INVENTION

The present invention overcomes the aforementioned drawbacks by providing a method for denoising medical images using a multiscale decomposition of the image using a multiscale total variation flow that is scaled such that a user-defined speed function can be used to control how quickly the decomposition can be achieved.

It is an aspect of the invention to provide a method for denoising an image using a multiscale total variation flow. An image to be denoised is provided, and a total variation flow image is computed by solving a multiscale total variation flow equation that includes a scaling parameter and the provided image. The total variation flow image is then stored as an updated version of the provided image. The multiscale total variation flow process is iteratively repeated until a stopping criterion is satisfied. The updated version of the image that satisfies the stopping criterion is then stored as a denoised image.

It is another aspect of the invention to provide a method for registering at least two images using a multiscale total variation flow. At least two images to be registered are provided. Initial registration parameters are determined using the provided images, and scale images are produced by using a multiscale total variation flow. The scale images are registered using the initial registration parameters, and the initial registration parameters are updated based on the performed registration. This process is iteratively repeated until a stopping criterion is satisfied. In each iteration, successively finer scale images are produced by using a multiscale total variation flow with a time parameter set to a shorter interval than in a preceding iteration.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
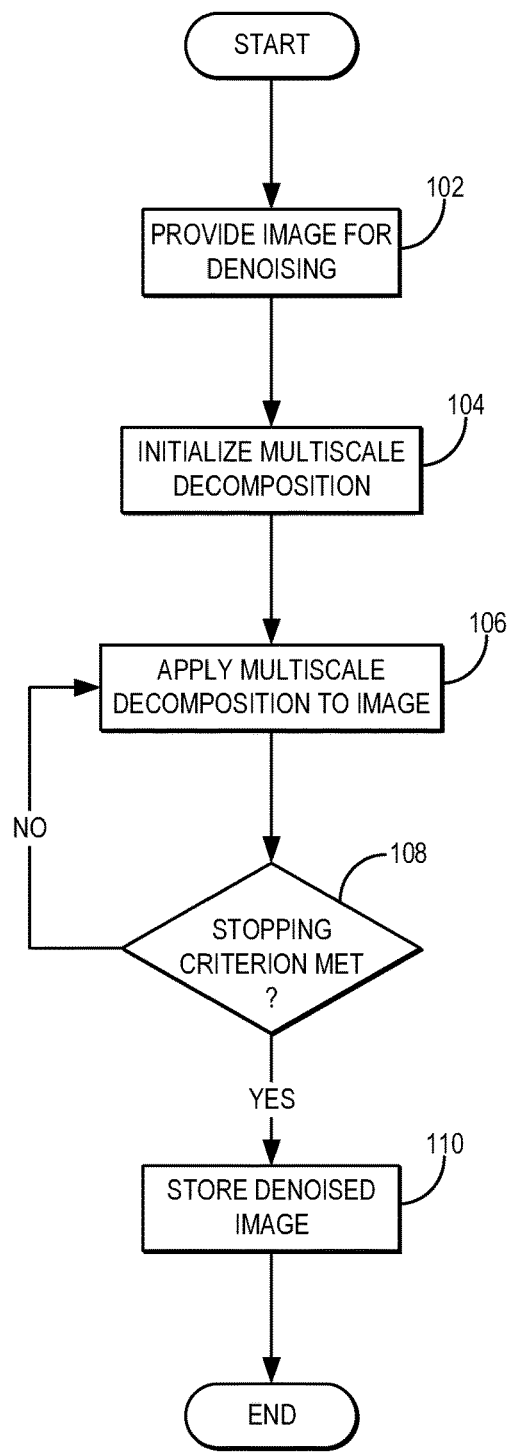
FIG. 1 is a flowchart setting forth the steps of an example of a denoising method using a multiscale decomposition of the input image.

Described here are systems and methods for representing multiple scales in an image using a multiscale total variation flow algorithm. In general, an iterative decomposition, such as a (TV, $L^2$) decomposition, of a given image, $f$, into a total variation ("TV") part, u, and a residual part, $f-u$, is provided. The TV part, u, is generally a function of bounded total variation, and the residual is generally a square integrable residual, such as an $L^2$ part. The decomposition can be successively applied to the TV-parts obtained at increasing scales. This approach yields a differential equation similar to the total variation flow and produces a multiscale representation of the given image. These systems and methods are useful for a number of image enhancement and image processing applications, such as the ones described below.

One example application of the multiscale total variation flow of an image includes fast denoising of medical images, where the noise is of smaller scale than useful structures in the image. Another example application of the multiscale decomposition includes accurate registration of medical, or other, images. In some embodiments of image registration applications, large- or coarse-scale images are registered first and the registration parameters determined from the large-scale images are then used as an initial estimate for registering successively finer scale images generated using the multiscale decomposition.

Another application of the multiscale total variation flow method of the present invention is for image restoration applications. For example, when data has been lost due to incomplete data acquisition, embedded annotation, or localized artifacts, then the missing data may need to be estimated. Typical techniques for restoring this missing data, such as linear interpolation, fail where there are strong edges, or where the gaps between known data are too large. Using the multiscale total variation method, fast inpainting can be achieved and used to estimate missing data.

Another application of the multiscale total variation flow method of the present invention is in image segmentation applications. A common and important difficulty with image segmentation methods is that the gradient map is noisy, which may yield many "false" edges that do not correspond to real object boundaries. By appropriately tuning the multiscale total variation flow, such as by adjusting an optional weighting parameter, objects can be smoothed while preserving boundaries between objects. In effect, this approach is capable of cleaning the gradient map to remove spurious edges.

Localization, or finding relevant objects in an image, can be viewed as a multiscale problem. In such an approach, a large-scale, highly smoothed, image is analyzed first to find a region-of-interest. Then, a smaller scale is used to find another region, and a smaller scale is then used to find another region or feature, and so on. Thus, using the multiscale total variation flow method of the present invention, an iterative segmentation with a different scale chosen at each iteration level can be used to determine the segmentation effectively. Moreover, the objects that are present at each scale are more likely to represent real features due to the global optimization.

The fast multiscale total variation flow technique is motivated by successive decomposition based on total variation minimization or weighted total variation minimization. Thus, the algorithm smoothes the input image at an increasing scale, thereby producing a multiscale total variation representation of the input image. Because noise is a small-scale component of an image, the proposed method can be used for denoising images. The denoising speed is determined by the user, making the algorithm well-suited for real-time applications. The proposed method inherits edge preserving properties from total variation flow. Using this property, a novel multiscale image registration algorithm can be designed, where corresponding scales in images are registered, thereby registering images efficiently and accurately. This edge-preserving property of the algorithm can be enhanced by introducing an appropriate weight into the multiscale total variation flow.

One of the earliest partial differential equation ("PDE")-based methods for denoising a given image, $f$, and for multiscale representation, is the heat equation, which is equivalent to Gaussian smoothing. Using the heat equation for denoising yields a family of images, $\{u(\cdot,t)\}_{t\geq 0}$, that can be viewed as smoothed versions of the image, $f$. In this linear setup, smoothing is implemented by a convolution with the two-dimensional Gaussian kernel; hence, small scale details are smoothed out. The family of images, $\{u(\cdot,t)\}_{t\geq 0}$, can be viewed as a multiscale representation of the image, $f$, because $u(\cdot, t)$ diffuses from the small scales in the image into increasingly larger scales.

Some variational methods also produce multiscale image representation while preserving edges. These techniques are based on minimizing a suitable energy. For example, the $(TV, L^2)$ decomposition of an image includes finding the minimizer, $u_\lambda$, for the following minimization problem:

$$u_\lambda := \arg\inf_u \left\{ \int_\Omega |\nabla| + \lambda \int_\Omega |f - u|^2 \right\}; \tag{1}$$

where the minimizer, $u_\lambda$, is a denoised version of the image with the scale of about $1/\lambda$. If the parameter $\lambda = \lambda_0$ in Eqn. (1) is selected to be very small, then an image, $u_{\lambda_0}$, is obtained and this image has a large fidelity term, $$\int_\Omega |f-u|^2 \tag{2}$$

On the other hand, if the scaling parameter, $\lambda_0$, is selected to be large, then the image, $u_{\lambda_0}$, thus obtained will be closer to the given image, $f$.

The method of the present invention decomposes the original image, $f$, using a large parameter, $\lambda_0$, in the $(TV, L^2)$ decomposition shown in Eqn. (1) in order to obtain an initial decomposition of the image, $f$, $$f = u_{\lambda_0} + v_{\lambda_0} \tag{3};$$

and then decomposes the image, $u_{\lambda_0}$, using a smaller scaling parameter, $\lambda_1 < \lambda_0$, to obtain the $(TV, L^2)$ decomposition of the image, $u_{\lambda_0}$, $$u_{\lambda_0} = u_{\lambda_1} + v_{\lambda_1} \tag{4}.$$

This process is iteratively continued, each time decomposing the TV-part, $u_{\lambda_{i+1}}$, of the resultant image, $u_{\lambda_i}$, with $\lambda_{i+1} > \lambda_i$, thus producing the following nonlinear multiscale decomposition:

$$u_{\lambda_N} = f - \sum_{i=0}^{N} v_{\lambda_i} = f + \sum_{i=0}^{N} \frac{1}{2\lambda_i} div\left(\frac{\nabla u_{\lambda_i}}{|\nabla u_{\lambda_i}|}\right). \tag{5}$$

The divergence term, $div(\nabla u_{\lambda_i}/|\nabla u_{\lambda_i}|)$, in Eqn. (5) comes from the Euler-Lagrange differential equation for the minimization in Eqn. (1). The multiscale representation in Eqn. (5) motivates the following integro-differential equation:

$$u(x, t) = f(x) + \int_0^t \frac{1}{2\lambda(s)} div\left(\frac{\nabla u(x, s)}{|\nabla u(x, s)|}\right) ds; \tag{6}$$

with $u(\cdot, t=0) := f$ as the initial condition and Neumann boundary conditions. Here, the function $\lambda(t)$ is any real-valued function that is monotone decreasing, and vanishing at infinity. Differentiating Eqn. (6) in time yields the following:

$$\frac{\partial u}{\partial t} = \mu(t) div\left(\frac{\nabla u}{|\nabla u|}\right); \tag{7}$$

where $u(\cdot, t=0) := f$ is imposed as the Neumann boundary condition and $\mu(t) \equiv 1/2\lambda(t)$ is referred to as the speed function. Eqn. (7) produces a multiscale flow and in some ways behaves as a total variation flow; thus, Eqn. (7) may be referred to as a multiscale TV flow. One of the important properties of Eqn. (7) is that the speed of denoising is directly proportional to the speed function, $\mu(t)$. The star-norm, which measures the noise and oscillation content in an image, may be defined as the dual of the TV-seminorm with respect to the $L^2$-inner product. Using this definition, the star-norm of the speed of the flow can be written as follows, $$\left\|\frac{\partial u}{\partial t}\right\|_* = \mu(t). \tag{8}$$

Thus, the speed of the denoising can be controlled using the speed function. This property can be exploited for real-time denoising of images by appropriately choosing the speed function, $\mu(t)$.

Alternatively, Eqn. (5) can be modified to account for a weighted total variation. That is, an iterative application of a $(TV_\alpha, L^2)$ decomposition can be applied to the given image, $f$, as follows:

$$u_{\lambda_{i-1}} = u_{\lambda_i} + \eta_{\lambda_i} \tag{9};$$

for $i=0, 1, 2, \ldots, N$ with $u_{\lambda_{-1}} = f$, and in which $$u_{\lambda_i} = \arg\inf_u \{|u|_{TV_\alpha(\Omega)} + \lambda_i \|u_{\lambda_{i-1}} - u\|_{L^2(\Omega)}\}; \tag{10}$$

where $\alpha: \Omega \to \Box$ is a weighting parameter; $\lambda_i$ is a "global" penalty parameter that is constant on the domain, $\Omega \subset \Box^2$, of the image, $f$. The Euler-Lagrange differential equation that formally characterizes the minimizers, $u_{\lambda_i}$, is given by the following:

$$u_{\lambda_i} = u_{\lambda_{i-1}} + \frac{1}{2\lambda_i} div\left(\frac{\alpha \nabla u_{\lambda_i}}{|\nabla u_{\lambda_i}|}\right); \tag{11}$$

with Neumann boundary condition. The global constant, $\lambda_i$, controls diffusion; however, diffusion may also need to be controlled locally based on the local information of the image. The weigh, $\alpha$, can be thought of as a "local" diffusion controlling function. By summing Eqn. (11) telescopically from $i=0, \ldots, N$, the following expression is obtained:

$$u_{\lambda_N} = f + \sum_{i=0}^{N} \frac{1}{2\lambda_i} div\left(\frac{\alpha \nabla u_{\lambda_i}}{|\nabla u_{\lambda_i}|}\right). \tag{11}$$

This motivates the following diffusion-controlled integro-differential equation similar to Eqn. (6):

$$u(x, t) = f(x) + \int_0^t \frac{1}{2\lambda(s)} div\left(\frac{\alpha(x) \nabla u(x, s)}{|\nabla u(x, s)|}\right) ds; \tag{13}$$

with $u(\cdot, t=0):=f$. Here, the function $\lambda(t)$ is a real-valued continuous monotone decreasing function that is vanishing at infinity. Differentiating Eqn. (13) with respect to time, the following weighted multiscale TV flow is obtained:

$$\frac{\partial u}{\partial t} = \mu(t) div\left(\frac{\alpha \nabla u(\cdot, t)}{|\nabla u(\cdot, t)|}\right); \tag{14}$$

where $\mu(t):=\frac{1}{2}\lambda(t)$ is the speed function. The partial differential equation ("PDE") in Eqn. (14) may be referred to as a multiscale $TV_\alpha$ flow, and produces a family of progressively smooth images, $\{u(t)\}_{t \geq 0}$. It is noted that Eqn. (14) is similar to Eqn. (7) but for the added weighting term, $\alpha$.

In the weighted multiscale total variation flow algorithm, the speed function can be defined via the $\alpha$-star norm, $\|\cdot\|_{\alpha*}$, which is the dual of the $TV_\alpha$-seminorm with respect to the $L^2$-inner product. The residual may be defined as, $$\eta(t):=f-u(t) \tag{15};$$

and the weighted multiscale total variation $(TV_\alpha)$ flow can be shown to have the following properties:

$$\left\|\frac{\partial u}{\partial t}\right\|_{\alpha*} = \mu(t). \tag{16}$$

Eqn. (16) indicates that the speed of denoising measured in the $\alpha$-star norm is determined by the speed function, $\mu(t)$. This suggests that fast denoising can be performed by selecting a rapidly increasing speed function.

In Eqn. (14), the speed function, $\mu(t)$, and the weight, $\alpha(x)$, need to be designed. The speed function, $\mu(t)$, is generally designed to be a monotone increasing continuous function. As an example, $\mu(t)$ may equal $1.01^t$. The weight $\alpha(x) \in [0,1]$ acts as a diffusion controlling function. To preserve edges in an image, $\alpha$ should be smaller near the edges and closer to one at relatively flat regions in the image. One example of a function that can achieve this is the following:

$$\alpha(s) = \frac{1}{\sqrt{1 + \left(\frac{s}{\beta}\right)^2}}; \tag{17}$$

with $s=|G_\sigma * \nabla f|$, where $G_\sigma$ is a Gaussian kernel with standard deviation, $\sigma$. The smoothing kernel should avoid mischaracterization of noise as edges; thus, the value of $\beta$ can be chosen to achieve this result. For example, $\beta=0.01$ can be used to satisfy conditions on $\alpha$, where the function, $f$, was scaled such that $f \in [0,1]$.

Having described methods for multiscale TV flow and weighted multiscale TV flow, in general, some example applications of these methods are now described. One such application is fast denoising of images. The flow in Eqn. (7) has many interesting properties, including edge-preserving smoothing and the dependence of the denoising speed on the user-defined speed function, $\mu(t)$.

The multiscale TV flow algorithm defined by Eqn. (7) can be used for denoising if an estimate of the noise variance, or equivalently the signal-to-noise ratio ("SNR"), is known. For denoising an image, $f$, the multiscale TV flow algorithm is initialized with $u(\cdot, t=0):=f$ and Eqn. (7) is solved using, for example, a finite difference scheme. At each time step, the variance of the residual, $f-u(\cdot,t)$, is measured, and the flow is terminated at $t=t_0$ when the variance of the residual is more than the estimated variance.

By way of example, the denoising algorithm using multiscale TV flow can be used to denoise an image with Gaussian noise. Referring now to FIG. 1, a flowchart setting forth the steps of an example of a method for denoising an image using a multiscale TV flow or weighted multiscale TV flow algorithm is illustrated. The method begins by providing an image to be denoised, as indicated at step 102. This image can be an image stored on a data storage or can be an image recently reconstructed from a medical imaging scan. For instance, step 102 may include acquiring medical imaging data with a medical imaging system, such as a magnetic resonance imaging ("MRI") system and reconstructing a noisy image therefrom. It is noted that the input data does not need to be two-dimensional images, but could generally be N-dimensional. By way of example, an x-ray fluoroscopy imaging sequence has two spatial dimensions and a temporal dimension, and may be processed using the method of the present invention as a three-dimensional data set.

After the image to be denoised has been provided, the algorithm is initialized, as indicated at step 104. Initialization includes selecting the initial image estimate, the speed function, $\mu(t)$, and when applicable, the weight, $\alpha$. By way of example, the initial image estimate is typically the provided image without any additional processing. The speed function, $\mu(t)$, may be selected as $1.01^t$ and the weight, $\alpha$, may be selected as noted above in Eqn. (17).

The multiscale, or weighted multiscale, total variation flow algorithm is then iteratively applied to the initial image estimate, as indicated at step 106. The multiscale TV flow concludes when a stopping criterion is satisfied, as indicated at decision block 108. An example of a stopping criterion is when the variance of the residual, $f-u(\cdot,t_0)$ becomes more than the noise variance, $\sigma_0$, from the initial image. In practice, the noise variance, $\sigma_0$, can be estimated empirically or statistically. The denoised image, $u(\cdot, t_0)$, is then stored, as indicated at step 110. The denoised image includes less noise than the initial image estimate, but without adversely noticeable diffusing of the sharp edge features in the image.

Figure 2:
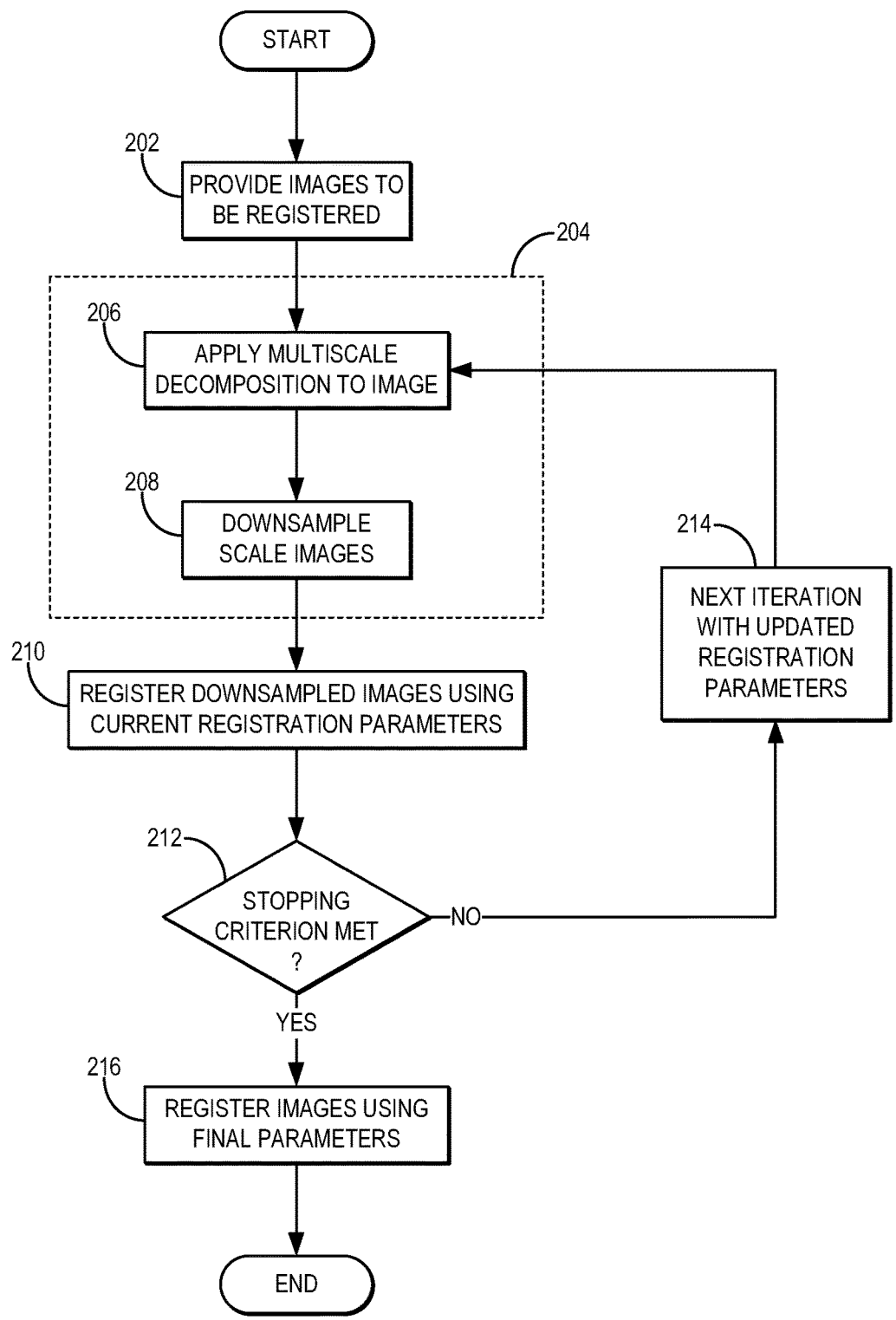
FIG. 2 is a flowchart setting forth the steps of an example of an image registration method that implements a multiscale decomposition of the input images.

The multiscale, or weighted multiscale, TV flow algorithm can also be used for image registration. Referring now to FIG. 2, an example of a method for using multiscale, or weighted multiscale, TV flow in the context of hierarchical image registration is illustrated. In this method, images to be registered are input to the algorithm and the larger scales in these images are registered first. The registration parameters thus obtained are then used as an initial estimate for the finer-scale images. In this manner, a robust and efficient registration can be achieved. This registration method can begin with providing the images to be registered, as indicated at step 202. As described above, these images could be previously reconstructed images that are stored in data storage, or may be images presently obtained in a medical imaging scan or other imaging process. It is also noted that the images need not be medical images, but could also be images obtained with another suitable imaging device. After the images to be registered have been identified, the image registration process proceeds as follows.

First, initial registration parameters, $\omega_0$, are selected. By way of example, the initial two-dimensional registration parameters may be derived by applying a conventional registration algorithm, such as a rigid transformation, to the input images. In rigid registrations, the registration parameters are as follows, $$\omega = (\theta, d_1, d_2) \qquad (18);$$

where $\theta$, is the angle of rotation and $d_1$ and $d_2$ are the translations in the x-direction and the y-direction, respectively. Using the initial registration parameters, registration of the large scale features in the images is performed, as indicated generally at 204. Registration includes applying the multiscale TV flow to the input images, as indicated at step 206. This produces coarse scale images, $u_f(\cdot, t_0)$ and $u_g(\cdot, t_0)$, using a large value for $t_0$. The coarse scale images are then downsampled, as indicated at step 208. The downsampled images are then registered using the initial registration parameters, $\omega_0$, as indicated at step 210, thereby resulting in an updated set of registration parameters, $\omega_i$, which will be used in the next iteration of the algorithm. This registration procedure is then repeated for finer scale images, $u_f(\cdot, t_i)$ and $u_g(\cdot, t_i)$, where $t_i < t_{i-1}$. Thus, the optimal transformation, $\omega_{i+1}$, from the current scale is iteratively applied as the initialization of the registration parameters for the next scale.

The registration is deemed to be successful when a stopping criterion is satisfied, as indicated at decision block 212. If the registration is not complete, then the updated registration parameters, $\omega_i$, are used in the next iteration of the algorithm, as indicated at step 214. If the stopping criterion is met, then the final registration parameters are stored and used to register the initial images, as indicated at step 216.

As another example, the multiscale, or weighted multiscale, TV flow algorithm can be used to align a three-dimensional prior roadmap image with two-dimensional images that are obtained in real-time. In general, to achieve this registration both the prior image and the real-time images are decomposed into coarse and fine scale feature images based on the multiscale TV flow algorithm described above. Specifically, the prior image, $f$, can be decomposed into a smooth component, $u$, and a residual component, $v = f - u$. To this end, a multiscale decomposition can generate a multiscale family $\{u_\lambda, v_\lambda\}$, where $\lambda$ denotes an algorithmic scale parameter. Using the multiscale TV flow algorithm described above, successively smoother images $u(\cdot,t)$ can be obtained. In subsequent iterations of the algorithm smoother images $u(\cdot,t)$ containing coarse scale features are obtained.

In some embodiments, the prior and the real-time images can subsequently be registered using a coarse-to-fine approach via minimizing a normalized gradient field ("NGF") distance metric between the images. An example of the NGF distance metric is described by E. Haber and J. Modersitzki, in "Intensity gradient based registration and fusion of multi-modal images," *Medical Image Computing and Computer Assisted Intervention* (MICCAI), 2006; 726-733. Coarse scale features extracted from the prior and real-time images are registered together first, and the resulting registration parameters are used as the initial guess for the alignment of finer scale features at the next level. This is repeated until a stopping criterion is satisfied, or until a predetermined number of iterations has been performed. For example, in some instances the algorithm may proceed for three levels of finer scale features.

Thus, a method for a multiscale total variation flow, which can be used for fast image denoising and image registration, has been provided. Both a non-weighted and a weighted algorithm are provided. The speed of the denoising can be changed by selecting different speed functions. This multiscale denoising is useful for images with small-scale noise. The multiscale total variation flow is also shown to have edge-preserving properties. The edge-preserving properties can be used to generate multiscale images without blurring main edge features. This multiscale total variation flow thus proves useful for hierarchical image registration of noisy images. Hierarchical registration using different scales is an efficient and robust registration method, and produced better registration results when compared to registration without the multiscale total variation flow. The algorithm can be used for rigid registration and, it is contemplated, for other types of registrations as well.

As noted above, the method of the present invention is also applicable to other applications, such as inpainting to replace missing data. In such an application, the weighted multiscale total variation flow can be used. In these applications, the data, $f$, is defined on a domain, $\Omega$ and the data is missing from a region, $D \subset \Omega$. The weighted multiscale total variation flow can be used to fill in the missing data. To this effect the speed of the multiscale total variation flow can be controlled to be very small where the data is known, and to be very high where the data is not known. The flow, $u(\cdot, t)$ converges to an agreeable solution to fill in the missing data.

In image segmentation applications, the multiscale total variation flow can be used to obtain a multiscale segmentation. In these applications, the multiscale total variation flow would be run for more time than in the denoising applications discussed above. Using this method a multiscale segmentation, whereby segmentation from coarse scales to finer scales, can be implemented.

An example of how such a multiscale total variation flow may be used for segmentation is as follows. First, the multiscale total variation flow may be run for a time, $t_0$, to obtain $u(\cdot, t_0)$, where $t_0$ is large. A segmentation algorithm would then be applied to this smoothed image, $u(\cdot, t_0)$. This process would be iteratively repeated $t_i < t_{i-1}$ to refine the segmentation.

The method of the present invention can also be implemented for image compression applications, in which data can be eliminated from some known locations. The multiscale total variation flow can then be run where the data is not missing. Then, while sending the image, a lot of the data can be thrown away, but still be reconstructed on the receiving end, as will be described below.

A possible scheme for image compression may include the following steps. First, the set of edges, $E \subset \Omega$, in an image are identified using an edge detection method. This edge data is then stored. A percentage of the data from the initial image is then removed on the set $\Omega \backslash E$. For example, up to seventy percent of the data may be removed using a predetermined mask, M. The remaining data along with the stored edge data is then communicated to the receiver of the data. At the receiving end, the mask, M, is known. Thus, the data on $\Omega \backslash E$ can be reconstructed using the multiscale total variation flow method of the present invention. The edge data, E, can then be added back to reconstruct the full image.

Figure 3:
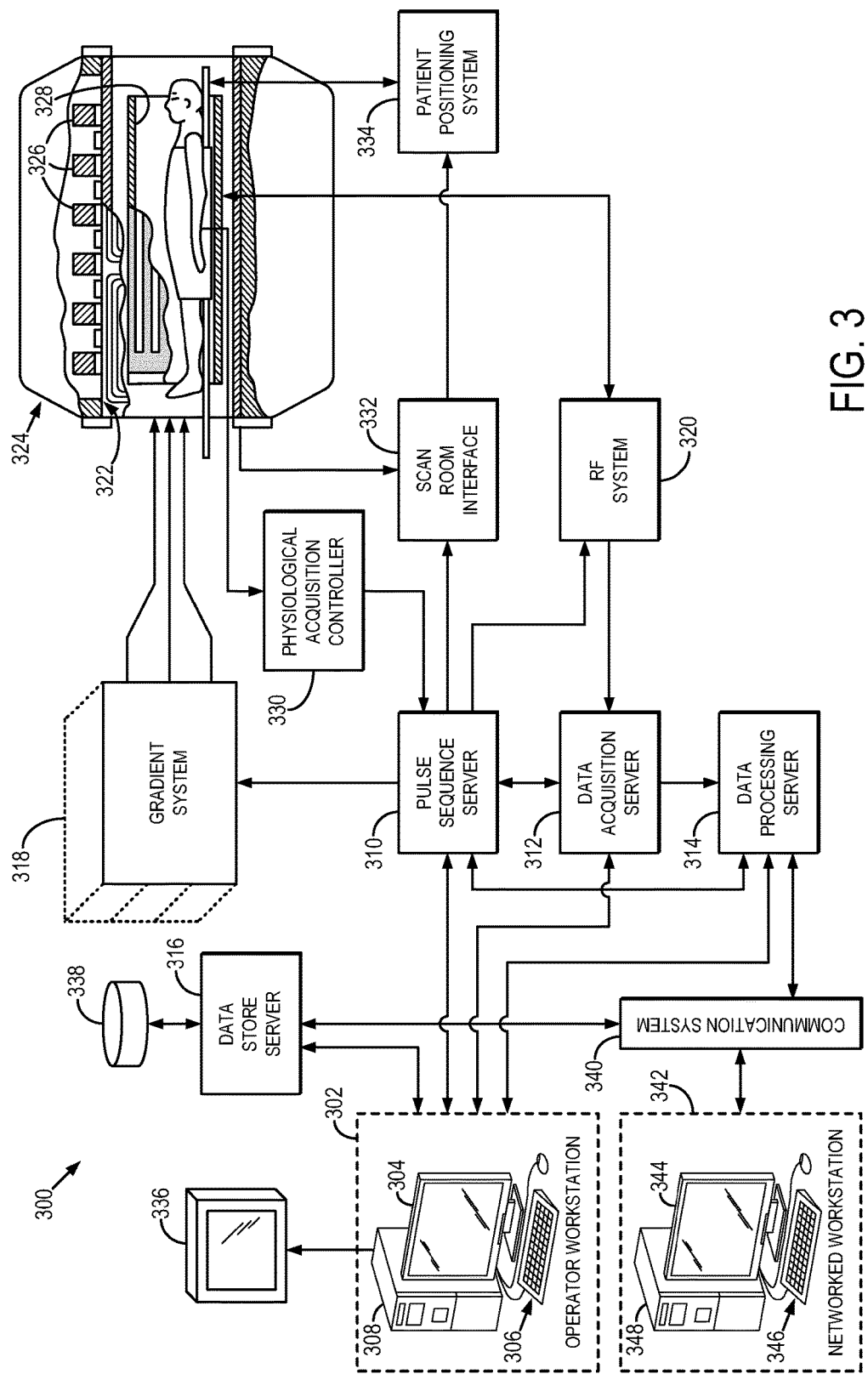
FIG. 3 is a block diagram of an example of a magnetic resonance imaging ("MRI") system.

Referring particularly now to FIG. 3, an example of a magnetic resonance imaging ("MRI") system 300 that may be used when practicing some embodiments of the present invention is illustrated. The MRI system 300 includes an operator workstation 302, which will typically include a display 304; one or more input devices 306, such as a keyboard and mouse; and a processor 308. The processor 308 may include a commercially available programmable machine running a commercially available operating system. The operator workstation 302 provides the operator interface that enables scan prescriptions to be entered into the MRI system 300. In general, the operator workstation 302 may be coupled to four servers: a pulse sequence server 310; a data acquisition server 312; a data processing server 314; and a data store server 316. The operator workstation 302 and each server 310, 312, 314, and 316 are connected to communicate with each other. For example, the servers 310, 312, 314, and 316 may be connected via a communication system 340, which may include any suitable network connection, whether wired, wireless, or a combination of both. As an example, the communication system 340 may include both proprietary or dedicated networks, as well as open networks, such as the internet.

The pulse sequence server 310 functions in response to instructions downloaded from the operator workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$, used for position encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil (not shown in FIG. 3), in order to perform the prescribed magnetic resonance pulse sequence. Responsive magnetic resonance signals detected by the RF coil 328, or a separate local coil (not shown in FIG. 3), are received by the RF system 320, where they are amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the scan prescription and direction from the pulse sequence server 310 to produce RF pulses of the desired frequency, phase, and pulse amplitude waveform. The generated RF pulses may be applied to the whole-body RF coil 328 or to one or more local coils or coil arrays (not shown in FIG. 3).

The RF system 320 also includes one or more RF receiver channels. Each RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \tag{19}$$

and the phase of the received magnetic resonance signal may also be determined according to the following relationship:

$$\varphi = \tan^{-1}\left(\frac{Q}{I}\right). \tag{20}$$

The pulse sequence server 310 also optionally receives patient data from a physiological acquisition controller 330. By way of example, the physiological acquisition controller 330 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, such that no data is lost by data overrun. In some scans, the data acquisition server 312 does little more than pass the acquired magnetic resonance data to the data processor server 314. However, in scans that require information derived from acquired magnetic resonance data to control the further performance of the scan, the data acquisition server 312 is programmed to produce such information and convey it to the pulse sequence server 310. For example, during prescans, magnetic resonance data is acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also be employed to process magnetic resonance signals used to detect the arrival of a contrast agent in a magnetic resonance angiography ("MRA") scan. By way of example, the data acquisition server 312 acquires magnetic resonance data and processes it in real-time to produce information that is used to control the scan.

The data processing server 314 receives magnetic resonance data from the data acquisition server 312 and processes it in accordance with instructions downloaded from the operator workstation 302. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 314 are conveyed back to the operator workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the operator workstation 302. The operator workstation 302 may be used by an operator to archive the images, produce films, or send the images via a network to other facilities.

The MRI system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 302, or in a different facility, such as a different healthcare institution or clinic.

The networked workstation 342, whether within the same facility or in a different facility as the operator workstation 302, may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may exchanged between the data processing server 314 or the data store server 316 and the networked workstations 342, such that the data or images may be remotely processed by a networked workstation 342. This data may be exchanged in any suitable format, such as in accordance with the transmission control protocol ("TCP"), the internet protocol ("IP"), or other known or suitable protocols.

Figure 4:
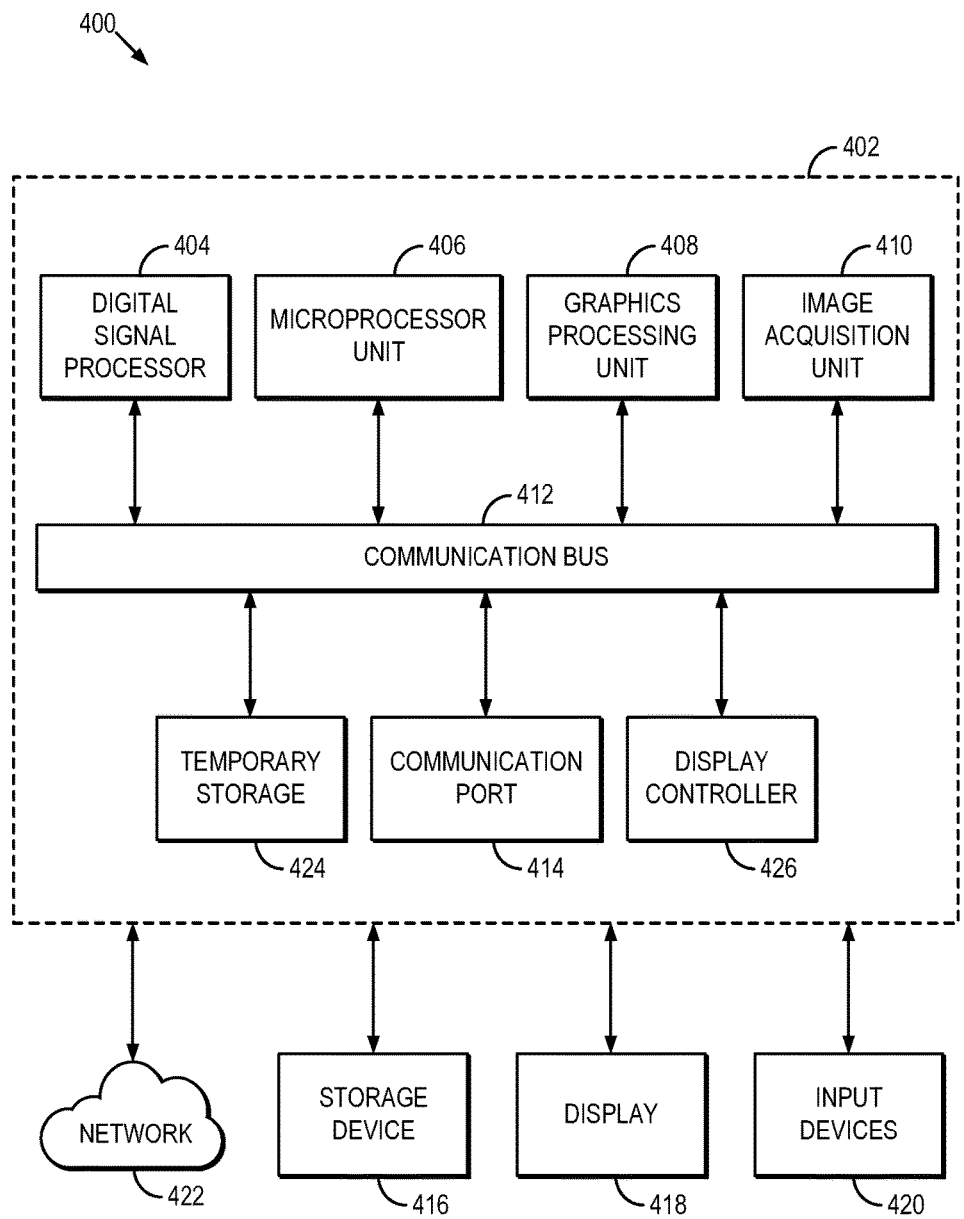
FIG. 4 is a block diagram of an example of a computer system that can be configured to implement some embodiments of the present invention.

Referring now to FIG. 4, a block diagram of an example computer system 400 for enhancing an image using a multiscale TV flow algorithm is illustrated. The image to be enhanced, which may be a digital image, is provided to the computer system 400 by a medical imaging system or another imaging system, and is received in an image processing unit ("IPU") 402.

In some embodiments, the IPU 402 can include one or more processing units. As an example, the IPU 402 may include one or more of a digital signal processor ("DSP") 404, a microprocessor unit ("MPU") 406, and a graphics processing unit ("GPU") 408. The IPU 402 also preferably includes an image acquisition unit 410 that is configured to electronically receive an image to be processed. The DSP 404, MPU 406, GPU 408, and image acquisition unit 410 are all coupled to a communication bus 412. As an example, the communication bus 412 can be a group of wires or a hardwire used for switching data between the peripherals or between any component in the IPU 402.

The DSP 404 can be configured to receive an image and processes the image to yield a digital image. The MPU 406 and GPU 408 can be configured to process the image in conjunction with the DSP 404. As an example, the GPU 408 can process image graphics. Also as an example, the MPU 406 can be configured to control operation of components in the IPU 402 and can include instructions to perform processing of the image on the DSP 404.

In some embodiments, the DSP 404 can be configured to process an image received by the IPU 402 in accordance with the multiscale TV flow algorithms described herein. Thus, the DSP 404 can be configured to enhance a received or stored image, register two or more received or stored images, compress a received or stored image, and segment a received or stored image.

The IPU 402 preferably includes a communication port 414 in electronic communication with other devices, which may include a storage device 416, a display 418, and one or more input devices 420. Examples of an input device 420 include, but are not limited to, a keyboard, a mouse, and a touch screen through which a user can provide an input.

The storage device 416 is configured to store digital images, whether those provided to the IPU 402 or those processed or enhanced images generated by the IPU 402. The display 418 is used to display images, such as images that may be stored in the storage device 416. Thus, in some embodiments, the storage device 416 and the display 418 can be used for displaying the digital image, both before and after enhancement, and for outputting other information.

The IPU 402 can also be in electronic communication with a network 422 to transmit and receive data, including images. The communication port 414 can also be coupled to the IPU 402 through a switched central resource, for example the communication bus 412.

The IPU 402 can also include a temporary storage 424 and a display controller 426. As an example, the temporary storage 424 can store temporary information. For instance, the temporary storage 424 can be a random access memory.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for denoising an image, the steps of the method comprising:
    a) providing an image to be denoised to a computer system;
    b) generating a smoothed image from the provided image by computing a total variation flow of the provided image according to a scale parameter using the computer system;
    c) updating the provided image by storing the smoothed image as an updated version of the provided image in a memory of the computer system;
    d) iteratively repeating steps b) and c) with the computer system until a stopping criterion is satisfied, wherein each repetition of step b) includes generating the smoothed image from the updated version of the provided image using a different scale parameter;
    e) storing the updated version of the provided image that satisfies the stopping criterion in step d) as a denoised image; and
    wherein a speed at which the stopping criterion is satisfied is controlled using a speed function that is a monotonically increasing continuous function.

2. The method as recited in claim 1, wherein the scale parameter controls a degree of denoising in the smoothed image and step d) includes selecting the different scale parameter as a scale parameter that is smaller than the scale parameter from a previous iteration.

3. The method as recited in claim 1, wherein the total variation flow computed in step b) is a weighted total variation flow that is weighted by a weighting value.

4. The method as recited in claim 3, wherein the weighting value is selected to preserve edge features in the provided image and the updated versions of the provided image.

5. The method as recited in claim 4, wherein the weighting value is selected to have values closer to zero near edge features and values closer to one in flat image regions.

6. The method as recited in claim 1, wherein the scale parameter is a denoising time.

7. The method as recited in claim 1, wherein step c) includes generating a residual image by computing a difference between the smoothed image and the provided image; and wherein the stopping criterion is satisfied in step d) when a variance of the residual image is more than a noise variance of the image provided in step a).

8. A method for denoising an image, the steps of the method comprising:
    a) providing an image to be denoised to a computer system;
    b) generating a smoothed image from the provided image by computing a total variation flow of the provided image according to a scale parameter using the computer system;
    c) updating the provided image by storing the smoothed image as an updated version of the provided image in a memory of the computer system;
    d) iteratively repeating steps b) and c) with the computer system until a stopping criterion is satisfied, wherein each repetition of step b) includes generating the smoothed image from the updated version of the provided image using a different scale parameter;
    e) storing the updated version of the provided image that satisfies the stopping criterion in step d) as a denoised image; and
    wherein the scale parameter is a denoising time.

9. The method as recited in claim 8, wherein the scale parameter controls a degree of denoising in the smoothed image and step d) includes selecting the different scale parameter as a scale parameter that is smaller than the scale parameter from a previous iteration.

10. The method as recited in claim 8, wherein the total variation flow computed in step b) is a weighted total variation flow that is weighted by a weighting value.

11. The method as recited in claim 10, wherein the weighting value is selected to preserve edge features in the provided image and the updated versions of the provided image.

12. The method as recited in claim 11, wherein the weighting value is selected to have values closer to zero near edge features and values closer to one in flat image regions.

13. The method as recited in claim 8, wherein a speed at which the stopping criterion is satisfied is controlled using a speed function that is a monotonically increasing continuous function.

14. The method as recited in claim 8, wherein step c) includes generating a residual image by computing a difference between the smoothed image and the provided image; and wherein the stopping criterion is satisfied in step d) when a variance of the residual image is more than a noise variance of the image provided in step a).

* * * * *